United States Patent [19]

Clarke et al.

[11] Patent Number: 5,525,652
[45] Date of Patent: Jun. 11, 1996

[54] DENTURE ADHESIVE

[75] Inventors: Hal C. Clarke, Elmont, N.Y.;
Hyung-Kook Ahn, East Brunswick, N.J.; Eddie Wong, New Providence, N.J.; Robert C. Gasman, Montville, N.J.; Alfred J. Smetana, Wayne, N.J.; Joseph Synodis, Summit, N.J.

[73] Assignee: Block Drug Company, Inc., Jersey City, N.J.

[21] Appl. No.: 288,586

[22] Filed: Aug. 10, 1994

[51] Int. Cl.$^6$ ........................................ C08F 8/42
[52] U.S. Cl. .............. 524/37; 524/549; 524/559; 525/327.8; 525/328.9; 525/367; 525/368; 525/369
[58] Field of Search .............. 525/327.8, 328.9; 524/549, 559, 37

[56] References Cited

U.S. PATENT DOCUMENTS

| | | | |
|---|---|---|---|
| 3,003,988 | 10/1961 | Germann | 260/33.6 |
| 4,138,477 | 2/1979 | Gaffar | 424/52 |
| 4,514,528 | 4/1985 | Dhabhar | 523/120 |
| 4,758,630 | 7/1988 | Shah | 525/207 |
| 4,910,247 | 3/1990 | Haldar | 524/400 |
| 5,073,604 | 12/1991 | Holeva | 525/327.8 |
| 5,298,534 | 3/1994 | Prosise | 523/120 |

FOREIGN PATENT DOCUMENTS

| | | |
|---|---|---|
| 140486 | 5/1985 | European Pat. Off. |
| 1492038 | 11/1977 | United Kingdom. |
| WO9210986 | 7/1992 | WIPO. |
| WO9210987 | 7/1992 | WIPO. |
| WO9210988 | 7/1992 | WIPO. |
| WO9222280 | 12/1992 | WIPO. |

OTHER PUBLICATIONS

Belaga, J. & Strauss, U., J. Phys. Chem 76 (2), 254–260 (1972).

*Primary Examiner*—Bernard Lipman
*Attorney, Agent, or Firm*—Ostrolenk, Faber, Gerb & Soffen

[57] ABSTRACT

A novel denture adhesive composition contains an adhesive mixture comprising sodium carboxymethyl cellulose and, either a partially neutralized sodium, magnesium, zinc mixed salt or a partially neutralized magnesium, zinc mixed salt of an alkyl vinyl ether maleic acid copolymer.

26 Claims, 5 Drawing Sheets

DENTURE ADHESIVE

BACKGROUND OF THE INVENTION

1. Field of the Invention

The invention relates to denture adhesives and to methods for making and using denture adhesives.

2. Description of Related Art

Ordinary removable dentures and dental plates function as a substitute for all or part of missing teeth ordinarily found in the mouth. While dentures are usually carefully fitted for the user, the fit can change over time, causing discomfort and slippage. In order to alleviate the discomfort and to control the slippage, a denture adhesive may be applied to the denture. The denture adhesive acts both as an adherent and as a gasket or cushion between the dentures and the gums of the denture wearer.

Denture adhesives are required to provide a diverse range of seemingly contradictory properties in an extraordinarily complex environment: the human mouth. Denture adhesives must develop a quick tack upon contact with the oral mucosa to prevent the denture from coming loose; they must also develop cohesive strength quickly when hydrated with moisture or saliva. They must also hold the denture in place for an indefinite period of time during use. They should only need to be applied once per day and should be nontoxic and organoleptically acceptable. They must not be easily washed out. But, denture adhesives must also easily release from the dentures and oral mucosa after use.

Several attempts have been made to fashion a denture adhesive using various polymer salts. One preferred polymer from the field is a copolymer of maleic anhydride and alkyl vinyl ether, sold under the Gantrez® trade name. This class of polymers was described as a possible denture adhesive in Germann et al. U.S. Pat. No. 3,003,988, which issued more than 30 years ago.

That patent describes synthetic, water sensitized but water insoluble, materials comprising mixed partial salts of lower alkyl vinyl ether—maleic anhydride copolymers for stabilizing dentures. The salts mentioned in the patent are a mixture of (a) calcium and (b) alkalies, including sodium, potassium and quaternary ammonium compounds in a 1:1 to 5:1 molar ratio. The calcium and alkali materials are added to the copolymer to form a mixed salt. The use of this class of materials has been described in a variety of other patents. Examples include U.S. Pat. Nos. 5,093,387, 5,037,924, 4,980,391 and 4,373,036, European Published Patent Application No. 406,643.

In order to provide additional adhesive and cohesive properties to denture adhesives made from Gantrez® polymers, one approach has been to manipulate the salt form of the copolymer. Examples can be found in WO 92/22280, WO 92/10988, WO 92/10987, and WO 92/10986.

One approach is found in U.S. Pat. No. 4,758,630 to Shah et al., issued Jul. 19, 1988. That patent is directed to denture adhesives having partial salts of zinc or strontium.

Another approach is reported in U.S. Pat. No. 5,073,604 to Holeva et al., issued Dec. 17, 1991. That patent is directed to a denture adhesive made from a partial salt of a Gantrez® polymer. The cations are zinc or strontium ions in combination with calcium, and optionally sodium, cations.

U.S. Pat. No. 5,298,534 to Prosise et al., issued Mar. 29, 1994 reports using Gantrez® salts of calcium, sodium, strontium, zinc, magnesium and potassium with boron cross-linked guar gum and an oil base as a carrier. The preferred mixed salt is a Ca/Na mixed salt. The guar gum is "critical" to claimed extended holding power and viscosity building properties.

Another approach has been to employ an adhesion adjuvant in the formulation or converting the copolymer into a terpolymer, and examples of these approaches can be found in U.S. Pat. No. 3,736,274, 5,037,924 and 5,093,387. Despite the efforts which have been put into improving the properties of maleic anhydride/alkyl vinyl ether type polymers and their salts, these formulations do not provide the full desired measure of adhesion, cohesion and resistance to washout from beneath the denture.

SUMMARY OF THE INVENTION

The principal object of the present invention therefore is to provide a new and improved denture adhesive composition that exhibits sufficient tack initially upon contact with oral mucosa, and builds up a cohesive strength for good hold characteristics when hydrated with moisture or saliva to be able to resist stresses such as those that occur upon mastication.

Another object of the invention is to provide an adhesive in which the improved adhesive retains its adhesive properties for prolonged periods of time and resists wash out.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides a denture adhesive comprising a sodium/magnesium/zinc salt or a magnesium/zinc salt, preferably in the form of partial salts, of a maleic acid/alkyl vinyl ether copolymer.

To further achieve the foregoing objects and in accordance with the purpose of the invention, the invention further provides a method for securing a removable dental device in the mouth comprising applying a denture adhesive comprising a zinc/magnesium salt or a sodium/magnesium/zinc salt, preferably in the form of partial salts, of a maleic acid/alkyl vinyl ether copolymer.

BRIEF DESCRIPTION OF THE DRAWINGS

While this specification concludes with claims particularly pointing out and distinctly claiming that which is regarded as the present invention, the objects and advantages of this invention may be more readily ascertained from the following description of a preferred embodiment when read in conjunction with the accompanying, drawings.

DESCRIPTION OF THE PREFERRED EMBODIMENTS

Reference will now be made in detail to the presently preferred embodiments of the invention.

The polymer salts of the present invention are the mixed partial salts of C1–C4 alkyl vinyl ether maleic acid copolymer. Methyl vinyl ether/maleic anhydride copolymer which has a specific viscosity larger than 1.2 in methyl ethyl ketone at 25° C., is the preferred copolymer. Most preferably, copolymers are selected from the copolymers set forth in United U.S. patent application No. 08/288,587, "Improved Denture Adhesive Composition," filed concurrently herewith, the disclosure of that application is incorporated herein by reference, and it lists Synodis, Smetana, Gasman, Wong and Clarke as inventors. While the copolymers of that invention are the preferred copolymers, this invention is not limited to the use of those copolymers.

The degree of substitution limits for alkyl vinyl ether/maleic acid (MVE/MA) partial salts of the invention are: (a) from about 5% to about 55% magnesium, more preferably from about 15% to about 45% magnesium, and most preferably from about 20% to about 40% magnesium; (b) from about 5% to about 65% zinc, more preferably from about 10% to about 60% zinc, and most preferably from about 15% to about 55% zinc; and (c) from about 0% to about 40% sodium, preferably from about 0% to about 35% sodium, and most preferably from about 0% to about 30% sodium.

This polymer salt is prepared by the partial neutralization of MVE/MA copolymer with the oxides and hydroxides of magnesium, zinc and sodium. When the salt is prepared, the metal compounds used react with the carboxylic acid groups on the copolymer and neutralize them. Preferably less than 100% of the carboxylic acid groups on the copolymer chain are neutralized. More preferably, the metal compounds neutralize from about 20% to about 95% of the carboxylic acid groups of the copolymer and most preferably from about 30% to about 90% of the carboxylic acid groups.

In choosing the alkaline, inorganic metal compound used to neutralize the carboxylic acid groups, the anion portion of the compound is not restricted, although it is preferably an oxide, hydroxide, carbonate or halide. Of the halides, chlorides are most preferred. In general, the oxides or hydroxides are preferred because of their ease of handling, availability and the generally innocuous nature of the by-products formed in their reaction with carboxylic acids.

To make the salt of the invention, a solution of the polymer is prepared, usually at an elevated temperature, and a solution or dispersion of the metal compounds is also prepared. After the heated polymer solution has cooled sufficiently, the solution or dispersion of metal compound and the polymer solution are combined and allowed to react. The product salt formed is dried, either in a tray or drum drier and preferably milled to less than about 100 mesh, then dispersed in a pharmacologically acceptable carrier to form the denture adhesive of this invention using techniques well known in the art.

MVE/MA copolymer is available from ISP Corporation in NJ, under the trade name Gantrez®. The polymer is available in a Gantrez-S series which is methyl vinyl ether/maleic acid and in a Gantrez AN series, which is methyl vinyl ether/maleic anhydride.

Denture adhesives of this invention can be formulated in the form of a powder, a liquid or a cream. The compositions also contain other active and non-active ingredients.

The denture adhesive composition of the present invention contains a denture adhesive effective amount of a denture adhesive salt and a pharmacologically acceptable carrier therefor. The denture adhesive salt usually comprises from about 15% to about 55% by weight of the denture adhesive composition. Preferably it is from about 18% to about 52% by weight of the denture adhesive composition, and most preferably from about 27% to about 36% by weight of the composition in a cream formulation and about 45% to about 55% by weight in a powder formulation.

The active ingredients in the adhesive are the Na/Mg/Zn partial salt of MVE/MA copolymer and sodium carboxymethyl cellulose gum. Non-active ingredient may include petrolatum, mineral oil, flavors, colors, preservatives, thickeners and non-toxic anticaking agent such as silica and talc.

In addition to the denture adhesive, the composition contains a pharmacologically acceptable carrier. The pharmacologically acceptable carrier contains conventional materials and if desired, can contain any adhesive adjuvants which have heretofore been used. For instance, the carrier may contain a carboxymethyl cellulose gum which is used for sensitizing the adhesive to moisture and enhancing the cohesive properties of the formulation and improving gel strength.

Carboxyethyl cellulose and carboxypropyl cellulose materials may also be used. When present, the cellulose gum preferably comprises from about 10% to about 30% by weight of the denture adhesive cream composition, more preferably from about 15% to about 25% and most preferably from about 20% to about 22% of the composition for a cream formula. In a powder formula, the cellulose gum preferably comprises from about 45% to about 55% of the composition. The cellulose gum may be present in the form of a full or partial salt, preferably a sodium salt.

Non-active ingredients that may be present in the carrier portion of the denture adhesive composition include thickening agents such as petrolatum, waxes, mineral oil and other oils; flavors such as synthetic flavor oils and/or oils derived from plants and fruits; colors suitable for food, drug and cosmetic use and known as FD&C colors; preservatives such as the parabens, benzoic acid and benzoates and the like; viscosity modifiers; and non-toxic anti-caking agents such as silica, magnesium stearate and talc.

In a cream formulation, the mineral oil or the like preferably comprises from about 10% to about 35%, preferably from about 12% to about 17% by weight of the composition, and petrolatum and the like preferably comprise from about 20% to about 50%, preferably from about 25% to about 45% by weight of the composition.

Preferred compositions for denture adhesive creme formulations using a 20% Mg/40% Zn/5% Na salt are as follows:

| Ingredient | Cream Weight % | Cream Weight % | Cream Weight % |
|---|---|---|---|
| Mg/Zn/Na Salt | 30% | 30% | 30% |
| CMC | 24% | 24% | 24% |
| Flavorant | 0.4% | — | 0.35% |
| Petrolatum | 29% | 29.45% | 29.05% |
| Mineral Oil | 16% | 16% | 16% |
| Preservative | 0.05% | 0.05% | 0.05% |
| Colorants | 0.05% | — | 0.05% |
| Fumed Silica | 0.5% | 0.5% | 0.5% |

Preferred compositions for a denture adhesive cream specially formulated to be compatible with a pump container and a powder formulation, both using a 20% Mg/40% Zn/5% Na salt, are as follows:

| Ingredient | Pump Cream Weight % | Powder Weight % |
| --- | --- | --- |
| Mg/Zn/Na Salt | 30% | 49.25% |
| CMC | 24% | 49.25% |
| Flavorant |  | 0.4% |
| Petrolatum | 3% |  |
| Mineral Oil | 40.90% |  |
| Preservative | 0.05% | 0.1% |
| Colorants | 0.05% |  |
| Fumed Silica | 0.5% | 1% |
| AC Polyethylene 6A | 1.5% |  |

EXAMPLE 1

900.40 grams of room temperature purified water were charged into a main reaction kettle equipped with a high speed stirrer. 73.38 g. of anhydrous MVE/MA copolymer were slowly added to the main mix kettle, with continuous mixing. The batch was heated to 85°–95° C.

250.11 grams of purified room temperature water was charged into a secondary kettle, and 7.52 grams of NaOH, 17.21 grams of ZnO and 1.89 grams of MgO were added slowly. All inorganic materials used as ingredients in the examples herein are USP grade anhydrous raw materials, unless otherwise noted. The secondary kettle was well mixed to form a homogeneous slurry. This slurry was slowly added into the main reaction kettle while mixing at high speed to prevent localized reaction. The temperature was reduced, and mixing was continued for two hours. The resulting solution was poured into shallow stainless steel drying trays, and the trays were placed in a hot air convection oven at 70° C. for 18–20 hours to give a dried salt. Although trays were used in this example, a drum drier would also be acceptable.

The dried Mg/Zn/Na Gantrez salt was then milled through a suitable mill and screened through a #100 mesh sieve. A one percent solution of the resulting powder would have a pH of from about 5 to about 7. This salt is a 10% Mg/45% Zn/20% Na salt of MVE/MA copolymer.

EXAMPLE 2 (Comparative)

A comparative salt was prepared by the same process as set forth in Example 1 except that a mole equivalent amount of Ca(OH)$_2$ was substituted for the amount of MgO used in Example 1. The resulting salt is a 10% Ca/45% Zn/20% Na salt of MVE/MA copolymer.

EXAMPLE 3

900.40 grams of room temperature purified water were charged into a main reaction kettle equipped with a high speed stirrer. 76.26 grams of anhydrous MVE/MA copolymer were slowly added to the main mix kettle, with continuous mixing. The batch was heated to 85°–95° C.

250.11 grams of purified room temperature water was charged into a secondary kettle, and 3.91 grams of NaOH, 15.89 grams of ZnO, and 3.94 grams of MgO were added slowly to the water. The secondary kettle was well mixed to form a homogeneous slurry. This slurry was then slowly added into the main reaction kettle while mixing at high speed to prevent localized reaction. The temperature was reduced, and mixing was continued for two hours. The resulting solution was poured into shallow stainless steel drying trays, and the trays were placed in a hot air convection oven at 70° C. for 18–20 hours to give a dried salt.

The dried Mg/Zn/Na Gantrez salt was then milled through a suitable mill and screened through a #100 mesh sieve. A one percent solution of the resulting powder would have a pH of from about 5 to about 7. This salt is a 20% Mg/40% Zn/10% Na salt of MVE/MA copolymer.

EXAMPLE 4 (Comparative)

A comparative salt was prepared by the same process as set forth in Example 3 except that a molar equivalent amount of Ca(OH)$_2$ was substituted for the amount of MgO used in Example 3. The resulting salt is a 20% Ca/40% Zn/10% Na salt of MVE/MA copolymer.

EXAMPLE 5

900.40 grams of room temperature purified water were charged into a main reaction kettle equipped with a high speed stirrer. 82.37 g. of MVE/MA copolymer were slowly added to the main mix kettle, with continuous mixing. The batch was heated to 85°–95° C.

250.11 grams of purified room temperature water was charged into a secondary kettle, and 7.52 grams of ZnO and 10.11 grams of MgO were added slowly to the water. The secondary kettle was well mixed to form a homogeneous slurry. This slurry was then slowly added into the main reaction kettle while mixing at high speed to prevent localized reaction. The temperature was reduced and mixing was continued for two hours. The resulting solution was poured into shallow stainless steel drying trays, and the trays were placed in a hot air convection oven at 70° C. for 18–20 hours to give a dried salt.

The dried Mg/Zn Gantrez salt was then milled through a suitable mill and screened through a #100 mesh sieve. A one percent solution of the resulting powder would have a pH of from about 4.5 to about 6.5. This salt is a 47.5% Mg/17.5% Zn salt of MVE/MA copolymer.

EXAMPLES 6–9

Figure 1:
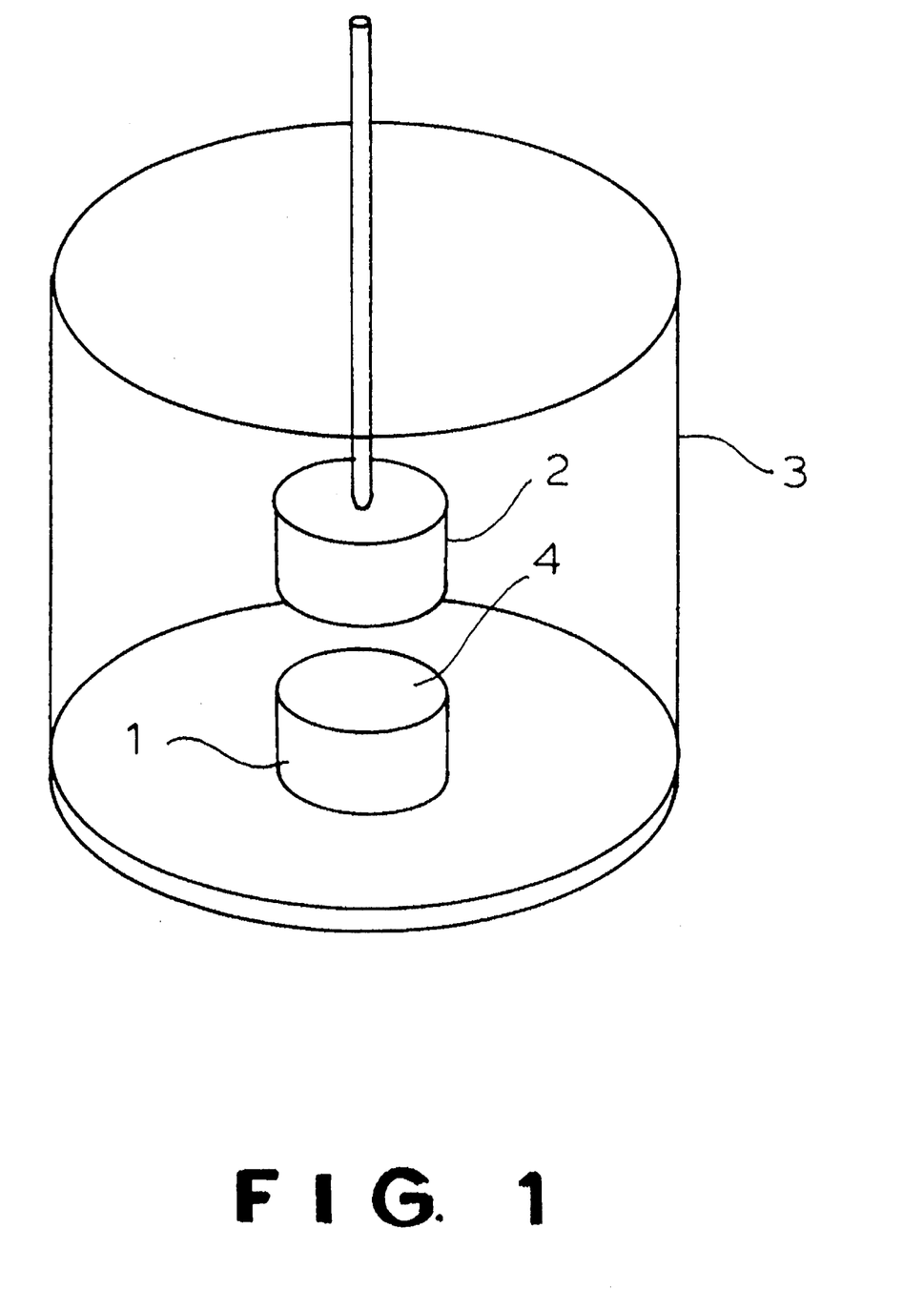
FIG. 1 shows the testing apparatus used to measure the adhesion strength of salts made in accordance with the invention.
Figure 2:
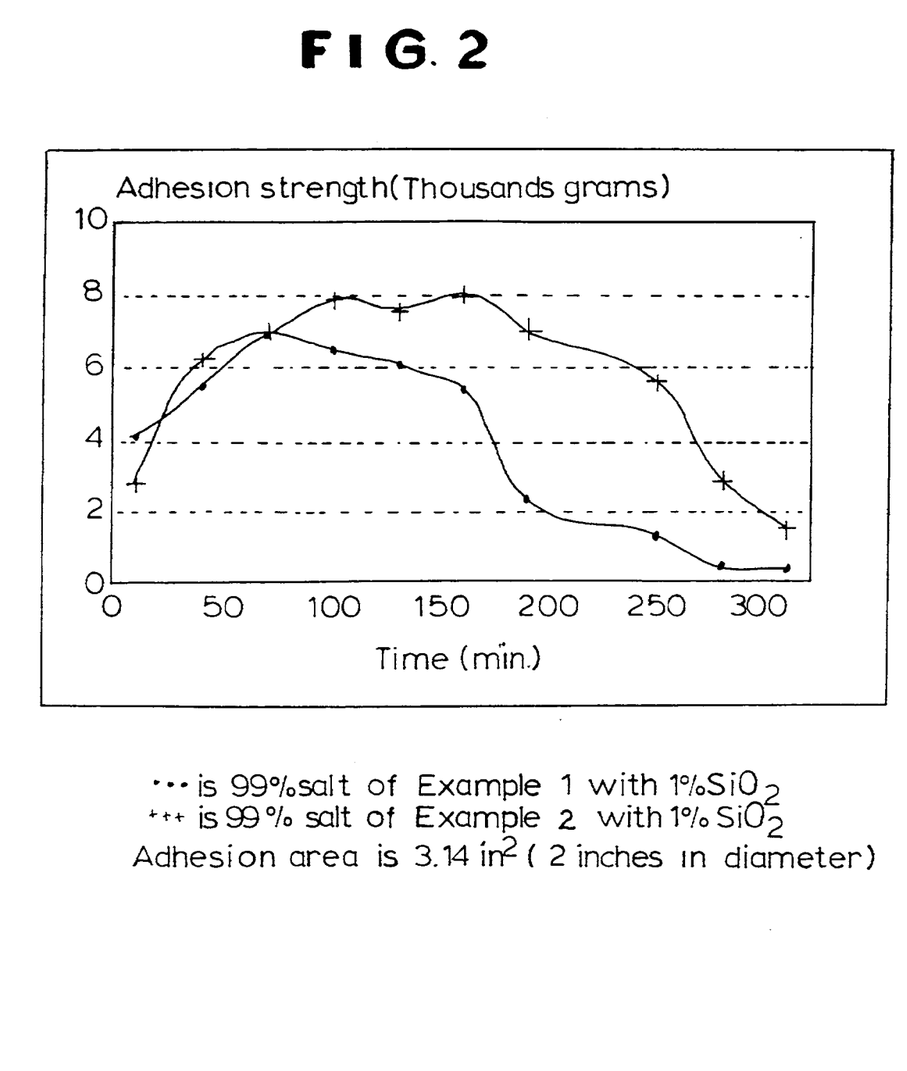
FIG. 2 is a graph of the adhesion strengths of the salts of Example 1 and of Example 2 over time.
Figure 3:
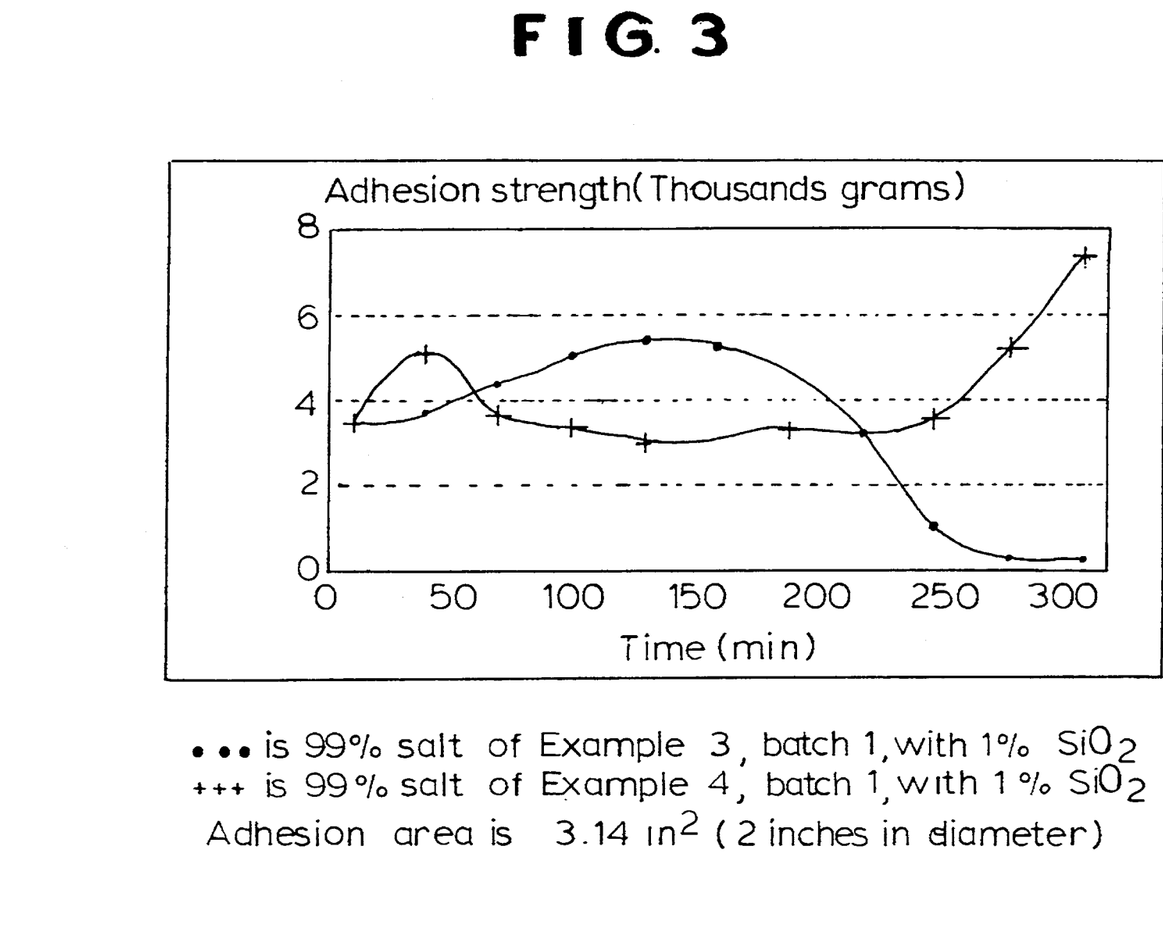
FIG. 3 is a graph of the adhesion strengths of the first batch of salts of Example 3 and of Example 4 over time.
Figure 4:
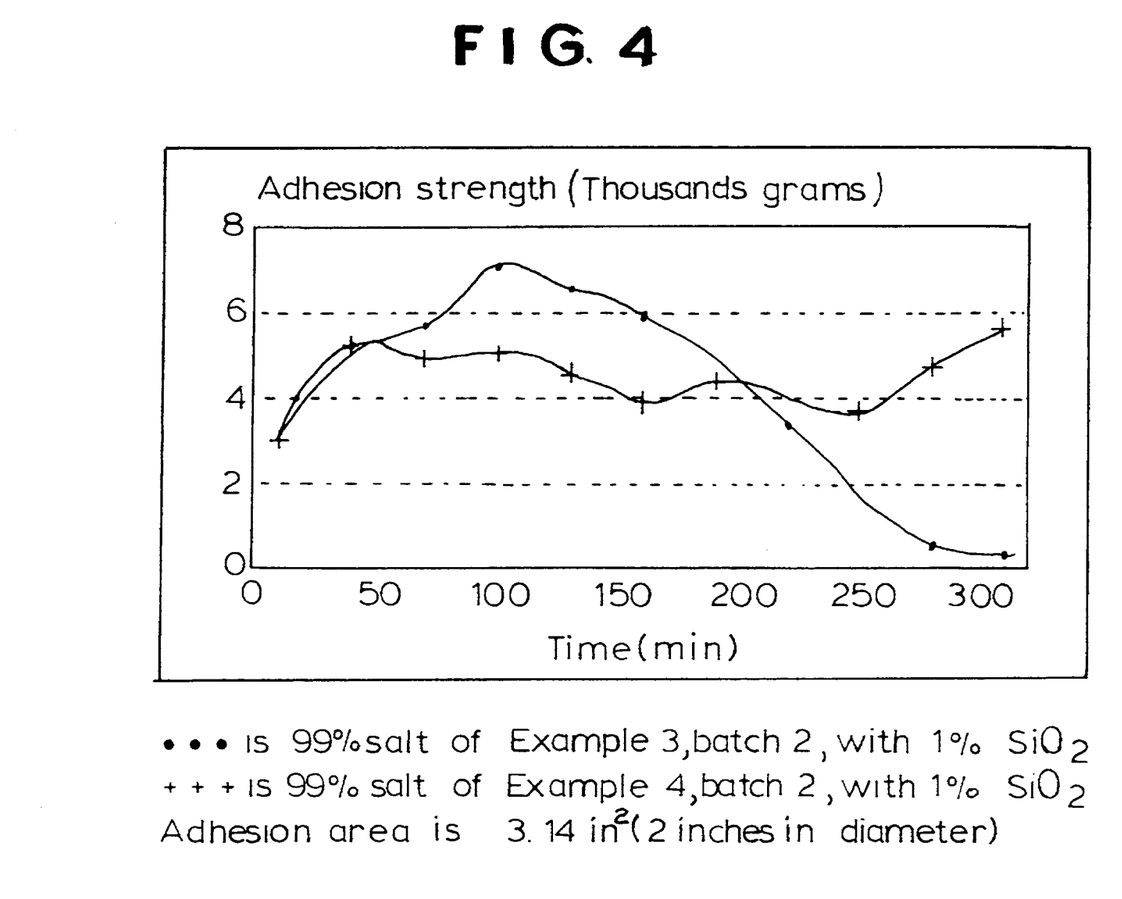
FIG. 4 is a graph of the adhesion strengths of the second batch of salts of Example 3 and of Example 4 over time.
Figure 5:
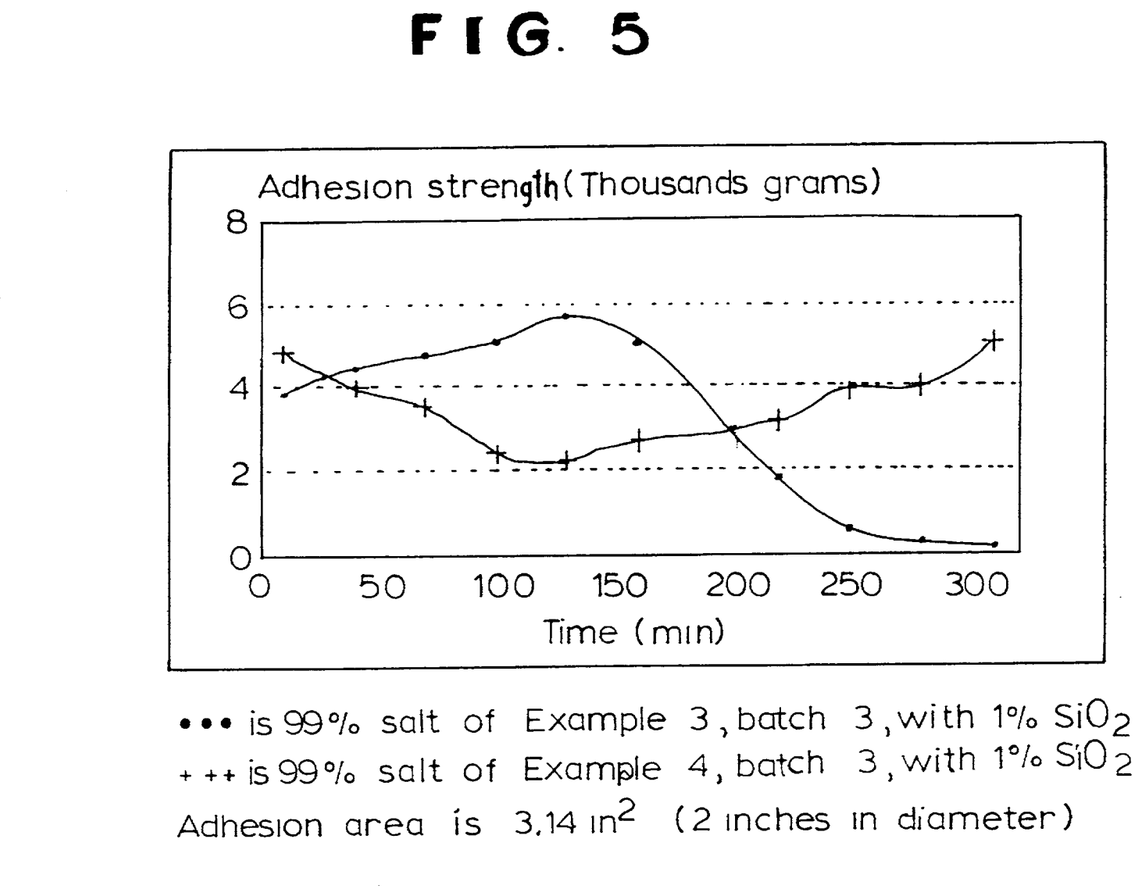
FIG. 5 is a graph of the adhesion strengths of the third batch of salts of Example 3 and of Example 4 over time.

Denture adhesive compositions were prepared from the finely milled salts of Examples 1–4 and were tested for adhesion strength using the mechanism shown in FIG. 1 in the following manner:

(a) 0.15 g of sample were placed on top of lower acrylic block 1;

(b) the sample was spread to cover the top of lower acrylic block 1, which had a diameter of 1.5 inches;

(c) upper block 2 was placed on top of lower block 1;

(d) water was placed in water bath 3 to just cover lower block 1 (the water will slowly penetrate between the blocks to hydrate the salt; a cloth 4 on the top of lower block 1 absorbs water during the test to hydrate the salts. The cloth is made from cotton and rayon and is commercially available from Mark V Laboratory);

(e) the sample was left for 10 minutes;

(f) 20 lbs. pressure was then applied for 5 seconds to upper block 2;

(g) the force required to separate the upper block 2 from lower block 1 was measured using an Instron Model #1122;

(h) after the blocks separated, they were left submerged in water for 10 seconds before replacing the upper block back on to the lower block so that the sample can absorb more water; and (i) steps (f), (g) and (h) were repeated after the times shown in the Tables.

The results are shown in Tables 1–7. In comparing the salt of Example 3 with the salt of Example 4, three different batches of each salt were tested.

TABLE 1

Example 1 Salt vs. Example 2 Salt

| Time (min.) | Adhesion Strength (units: g/3.14 in.$^2$) | |
|---|---|---|
| | Example 1 Salt | Example 2 Salt |
| 10 | 4086 | 2769 |
| 40 | 5448 | 6220 |
| 70 | 6855 | 6992 |
| 100 | 6492 | 7899 |
| 130 | 6084 | 7582 |
| 160 | 5403 | 8081 |
| 220 | 2361 | 7082 |
| 250 | 1362 | 5630 |
| 280 | 499 | 2906 |
| 310 | 454 | 1589 |

TABLE 2

Adhesion Strength of Example 3 Salt (1st batch)

| Time (minutes) | Adhesion Strength (units: g/3.14 in.$^2$) | | |
|---|---|---|---|
| | 1st run | 2nd run | Average |
| 10 | 3405 | 3223 | 3314 |
| 40 | 2815 | 4585 | 3700 |
| 70 | 3904 | 4767 | 4336 |
| 100 | 4994 | 4994 | 4994 |
| 130 | 5857 | 4767 | 5312 |
| 160 | 5811 | 4540 | 5176 |
| 220 | 4631 | 1725 | 3178 |
| 250 | 1589 | 499 | 1044 |
| 280 | 227 | 227 | 227 |
| 310 | 182 | 227 | 230 |

TABLE 3

Adhesion Strength of Example 4 Salt (1st batch)

| Time (min.) | Adhesion Strength (units: g/3.14 in.$^2$) | | |
|---|---|---|---|
| | 1st run | 2nd run | Average |
| 10 | 3450 | 3360 | 3405 |
| 40 | 5312 | 4903 | 5108 |
| 70 | 4358 | 2951 | 3655 |
| 100 | 3269 | 3405 | 3337 |
| 130 | 3042 | 2906 | 2974 |
| 160 | 2996 | N.A. | N.A. |
| 190 | 3223 | 3314 | 3269 |
| 220 | N.A. | 3904 | N.A. |
| 250 | 2588 | 4540 | 3564 |
| 280 | 4495 | 5857 | 5174 |
| 310 | 5993 | 8626 | 7310 |

TABLE 4

Adhesion Strength of Example 3 salt (2nd batch)

| Time (min.) | Adhesion Strength (units: g/3.14 in.$^2$) | | |
|---|---|---|---|
| | 1st run | 2nd run | Average |
| 10 | 3178 | 2906 | 3042 |
| 40 | 4994 | 5130 | 5062 |
| 70 | 6084 | 5266 | 5675 |
| 100 | 6810 | 7355 | 7083 |
| 130 | 6084 | 6946 | 6515 |
| 160 | 6628 | 5266 | 5947 |
| 190 | N.A. | 2724 | N.A. |
| 220 | 5539 | 1135 | 3337 |
| 250 | 2633 | N.A. | N.A. |
| 280 | 772 | 272 | 522 |
| 310 | 363 | 227 | 295 |

TABLE 5

Adhesion Strength of Example 4 Salt (2nd batch)

| Time (min.) | Adhesion Strength (unit: g/3.14 in.$^2$) | | |
|---|---|---|---|
| | 1st run | 2nd run | Average |
| 10 | 2951 | 3087 | 3019 |
| 40 | 5630 | 4858 | 5244 |
| 70 | 5130 | 4676 | 4903 |
| 100 | 4767 | 5403 | 5085 |
| 130 | 4495 | 4540 | 4518 |
| 160 | 2951 | 4767 | 3859 |
| 220 | 3995 | 4631 | 4313 |
| 250 | 3768 | 3541 | 3655 |
| 280 | 3814 | 5539 | 4677 |
| 310 | 5403 | 5811 | 5607 |

TABLE 6

Adhesion Strength of Example 3 Salt (3rd batch)

| Time (min.) | Adhesion Strength (units: g/3.14 in.$^2$) | | |
|---|---|---|---|
| | 1st run | 2nd run | Average |
| 10 | 3133 | 4449 | 3791 |
| 40 | 3768 | 5085 | 4427 |
| 70 | 4631 | 4812 | 4722 |
| 100 | 5085 | 4994 | 5039 |
| 130 | 5947 | 5357 | 5652 |
| 160 | 6265 | 3723 | 4994 |
| 220 | 1226 | 2270 | 1748 |
| 250 | 409 | 726 | 568 |
| 280 | 182 | 318 | 250 |
| 310 | 136 | 227 | 182 |

TABLE 7

Adhesion Strength of Example 4 Salt (3rd batch)

| Time (min.) | Adhesion Strength (units: g/3.14 in.$^2$) | | |
|---|---|---|---|
| | 1st run | 2nd run | Average |
| 10 | 4812 | 4812 | 4812 |
| 40 | 4177 | 3768 | 3973 |
| 70 | 3587 | 3360 | 3473 |
| 100 | 3133 | 1589 | 2361 |
| 130 | 2088 | 2225 | 2157 |
| 160 | 2497 | 2724 | 2611 |
| 220 | 3541 | 2633 | 3087 |

TABLE 7-continued

Adhesion Strength of Example 4 Salt (3rd batch)

| Time (min.) | Adhesion Strength (units: g/3.14 in.$^2$) | | |
|---|---|---|---|
| | 1st run | 2nd run | Average |
| 250 | 3768 | 3904 | 3836 |
| 280 | 4313 | 3450 | 3882 |
| 310 | 5221 | 4676 | 4949 |

EXAMPLE 10

900.40 grams of room temperature purified water were charged into a main reaction kettle equipped with a high speed stirrer. 77.80 grams of MVE/MA copolymer were slowly added to the main mix kettle and mixing was continued during addition of the copolymer. The reaction kettle was maintained at 85°–95° C.

250.11 grams of purified room temperature water was added to a second kettle, and 3.99 grams of NaOH, 12.18 grams of ZnO and 6.03 grams of MgO were also added to the second kettle. The combination was mixed well until it formed a homogeneous slurry. The slurry was added slowly to the main reaction kettle while high speed mixing was maintained to prevent localized reaction. The temperature was reduced, and mixing was continued for two hours. The resulting solution was transferred to shallow stainless steel drying trays, and the trays were placed in a hot air convection oven at 70° C. for 18–20 hours. The dried Mg/Zn/Na Gantrez salt was then milled through a suitable mill and then screened through a #100 mesh sieve. A one percent solution of the powder would have a pH of from about 5 to about 7. This salt is a 30% Mg/30% Zn/10% Na salt of MVE/MA copolymer.

EXAMPLE 11

900.40 grams of room temperature purified water were charged into a main reaction kettle equipped with a high speed stirrer. 76.27 grams of MVE/MA copolymer were slowly added to the main mix kettle and mixing was continued during addition of the copolymer. The reaction kettle was maintained at 85°–95° C. 250.11 grams of purified room temperature water was added to a second kettle, and 3.91 grams of NaOH, 11.94 grams of ZnO and 7.88 grams of MgO were also added to the second kettle. The combination was mixed well until it formed a homogeneous slurry. The slurry was added slowly to the main reaction kettle while high speed mixing was maintained to prevent localized reaction. The temperature was reduced, and the mixing was continued for two hours. The resulting solution was transferred to shallow stainless steel drying trays, and the trays were placed in a hot air convection oven at 70° C. for 18–20 hours. The dried Mg/Zn/Na Gantrez salt was then milled through a suitable mill and then screened through a #100 mesh sieve. A one percent solution of the powder would have a pH of from about 5 to about 7. This salt is a 40% Mg/30% Zn/10% Na salt of MVE/MA copolymer.

EXAMPLES 12–19

Salt from the foregoing examples were combined with silica (1% based on the combination) and tested for adhesion as described above. The results are sets forth in FIGS. 2 through 5, respectively, and in each case the salt of the invention is shown by the dots and the comparative salt is shown by the crosses.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

What is claimed is:

1. A denture adhesive composition comprising a denture adhesive effective amount of a denture adhesive salt and a pharmacologically acceptable carrier therefor in which the denture adhesive salt is a mixed partial salt of a copolymer of maleic acid or anhydride and an alkyl vinyl ether, wherein the cations of said salt comprise zinc and magnesium ions.

2. The denture adhesive of claim 1, wherein said cations further comprise sodium ions.

3. The denture adhesive composition of claim 1, wherein the alkyl moiety is methyl.

4. The denture adhesive composition of claim 1, wherein said copolymer salt comprises from about 18% to about 52% of said denture adhesive.

5. The denture adhesive composition of claim 1, in the form of a cream.

6. The denture adhesive composition of claim 5, wherein said copolymer salt comprises from about 27% to about 36% by weight of said denture adhesive composition.

7. The denture adhesive composition of claim 1, in the form of a powder.

8. The denture adhesive composition of claim 7, wherein said copolymer salt comprises about 50% of said denture adhesive composition.

9. The denture adhesive composition of claim 1, further comprising from about 10% to about 30% of a carboxymethyl cellulose gum.

10. The denture adhesive composition of claim 9, wherein the gum is sodium carboxymethyl cellulose gum.

11. The denture adhesive composition of claim 10, wherein said sodium carboxymethyl cellulose gum comprises from about 15% to about 53% of said denture adhesive composition.

12. The denture adhesive of claim 1 in the form of a liquid.

13. The denture adhesive of claim 1 in the form of a pump compatible fluid.

14. A denture adhesive composition consisting essentially of a denture adhesive effective amount of a denture adhesive zinc and magnesium mixed partial salt of a copolymer of maleic acid or anhydride and an alkyl vinyl ether, and a pharmacologically acceptable carrier therefor.

15. The denture adhesive of claim 14, wherein the cations of said mixed salt further contain sodium ions.

16. The denture adhesive of claim 14, wherein the alkyl moiety is methyl.

17. The denture adhesive of claim 14, wherein said copolymer salt is about 18 to about 52% of the denture adhesive composition.

18. The denture adhesive of claim 14, in the form of a cream.

19. The denture adhesive of claim 18, wherein said copolymer salt is about 27 to about 36% of the denture adhesive composition.

20. The denture adhesive of claim 14, in the form of a powder.

21. The denture adhesive of claim 20, wherein said copolymer salt is about 50% of said denture adhesive composition.

22. The denture adhesive of claim 14, in the form of a liquid.

23. The denture adhesive of claim 14, in the form of a pump compatible fluid.

24. The denture adhesive composition of claim 14, further containing from about 10% to about 30% of a carboxymethyl cellulose gum.

25. The denture adhesive composition of claim 24, wherein the gum is sodium carboxymethyl cellulose gum.

26. The denture adhesive composition of claim 25, wherein said sodium carboxymethyl cellulose gum comprises from about 15% to about 53% of said denture adhesive composition.

* * * * *